United States Patent [19]

Rotella

[11] 4,425,713

[45] Jan. 17, 1984

[54] POSTUREOMETER

[76] Inventor: Sam S. Rotella, 982 N. Brookside Dr., Lewiston, N.Y. 14092

[21] Appl. No.: 411,590

[22] Filed: Aug. 25, 1982

[51] Int. Cl.³ .......................... G01B 5/20; A61B 5/10
[52] U.S. Cl. .................................. 33/174 D; 128/774
[58] Field of Search ......................... 33/174 D, 143 C; 128/774, 781

[56] References Cited

U.S. PATENT DOCUMENTS 3,955,285  5/1976  Moeckl ............................. 33/174 D
4,036,213  7/1977  Gregory .......................... 33/174 D

FOREIGN PATENT DOCUMENTS 403343  6/1922  Fed. Rep. of Germany ... 33/174 D
742944  10/1943  Fed. Rep. of Germany ... 33/174 D Primary Examiner—Willis Little

[57] ABSTRACT

This postureometer instrument is designed to measure, in inches and degrees, posture deviations of the human body. Primarily, it includes a base with a calibrated post, having a multiple number of adjustable pins for contact with the spinal column. It further includes a pair of elevatable yokes on the post, which are calibrated in degrees of angle, and include spaced arms having calibrated and adjustable pins for measuring various posture deviations.

2 Claims, 1 Drawing Figure

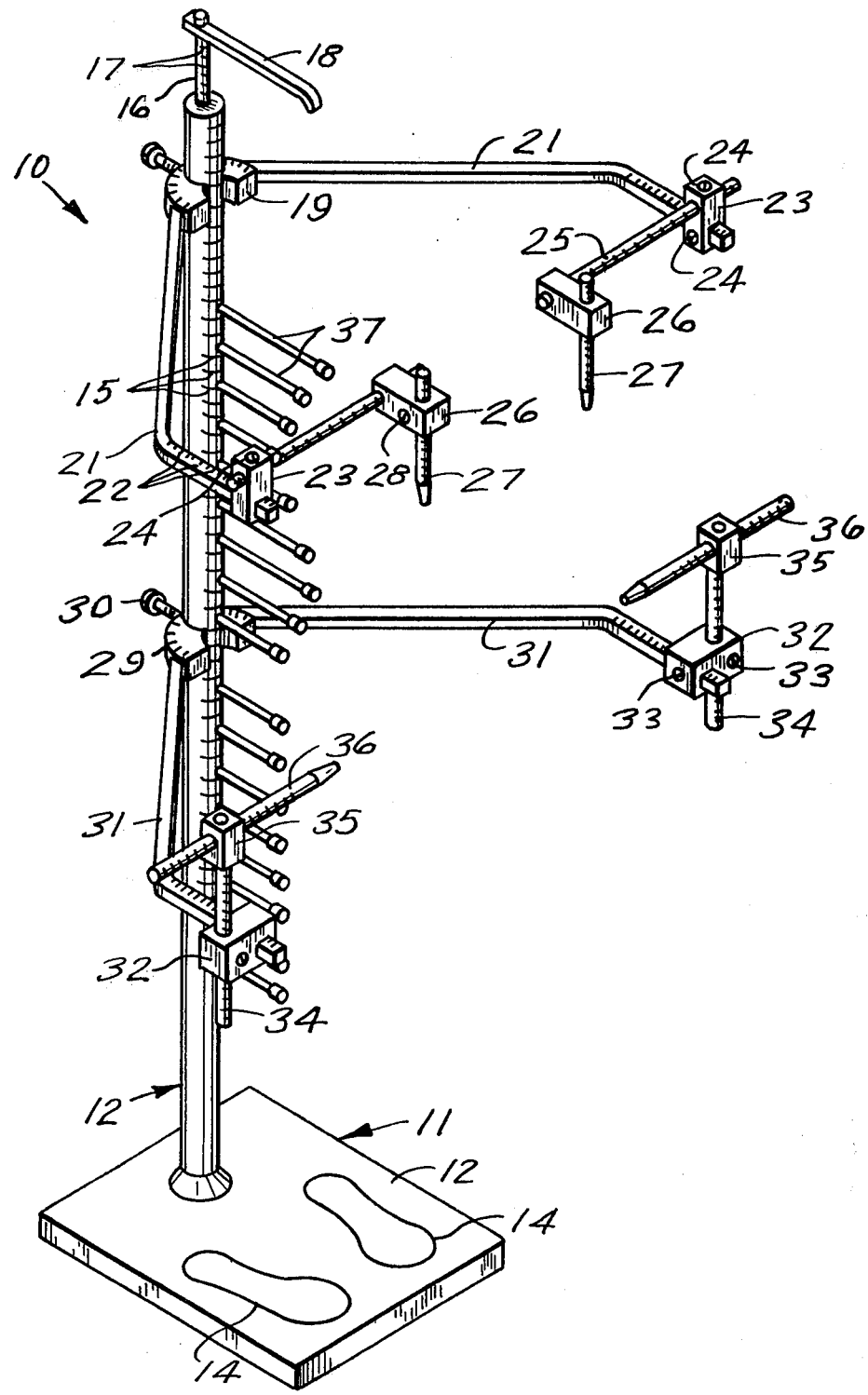

POSTUREOMETER

This invention relates to medical measuring instruments, and more particularly, to a postureometer.

The principal object of this invention is to provide a postureometer, which will measure, in inches and degrees, posture deviations for the following:
1. Shoulder rotation
2. Shoulder drop
3. Scoliosis
4. Kyphosis
5. Lordosis
6. Pelvic tilt
7. Pelvic rotation Another object of this invention is to provide a postureometer, which will include a base member with positions for the feet of a patient inscribed thereon, and a calibrated post will be secured to the base member, having an elevatable arm for indicating the height of the patient.

A further object of this invention is to provide a postureometer, which will include a pair of elevatable and forked arms, each having means, adjustable and calibrated in inches and degrees, for accurate measurement.

Other objects of the present invention are to provide a Postureometer, which is simple in design, inexpensive to manufacture, rugged in construction, easy to use and efficient in operation.

These, and other objects, will be readily evident, upon a study of the following specification, and the accompanying drawing, wherein:

The drawing is perspective, and is the sole view of the present invention.

According to this invention, an instrument 10 is shown to include a rectangular base member 11, having a tubular post 12, fixedly secured, in a suitable manner, to the top surface 13, which includes inscribed foot positions 14, for the placement of the feet of the person to be measured. Post 12 includes a plurality of equally spaced-apart spline projections 15 on its outer periphery, for measurement in inches of elevation, and a rod or shaft 16 is telescopingly received in the upper end of post 12, and is calibrated in inches by the spline projections 17 on the outer periphery of rod 16, and an arm 18 is fixedly secured to the top portion of rod 16 in a suitable manner. Arm 18, and its attached rod 16, is elevatable within post 12, so as to measure the height of a person being otherwise measured, when he is standing on the top surface 12 of the base member 11, the method used being common in the art.

A "C"-shaped upper yoke 19 is elevatably received on the outer periphery of post 12, and is rendered secured at any desired elevation, by a self-contained set screw 20 received in its center. A pair of angularly disposed arms 21 are fixedly secured, in a suitable manner, to the outer arcuate periphery of upper yoke 19, and the ends of arms 21 include inch calibrations 22, and the upper face of upper yoke 19 is calibrated in degrees, for angle measurements of the patient. Slideably secured to the ends of arms 21 is a rectangular block 23, that includes a pair of spring locks 24, which are common in the art. An inch calibrated and horizontally slideable pin 25 is slideably received in one end of each block 23, and is held in place, at any desired graduation, by one of the spring locks 24, and the other spring lock 24 enables block 23 to be set at any inch graduation on the arm 21. Another block 26 is fixedly secured to an end of pin 25 of each arm 21, and each block 26 includes an inch calibrated vertical pin 27, which is elevatable in blocks 26, and is held stationary at any desired calibration by means of a spring lock 28.

A lower yoke 29 is similar to upper yoke 19, and includes a set screw 30, for rendering it secure to post 12 at any desired elevation. Yoke 29 also includes arms 31, which are similar to arms 21 of yoke 19, and the ends of arms 31 are slideably adjustable within a block 32. The blocks 32 are held in any desired calibration position on arm 31 by means of a spring lock 33, and the second spring lock 33 of blocks 32 serves to hold a vertically slideable pin 34 in any desired elevation within blocks 32. A block 35 is fixedly secured to the upper ends of each of the pins 34 in a suitable manner, and a horizontally slideable and calibrated pin is adjustably secured in blocks 35 by suitable spring locks, not shown. A plurality of headed and calibrated pins 37 are also included, and are threaded into the front of post 12, for adjustable contact with the spine of the patient, and the functions of the aforementioned will hereinafter be described.

It shall also be noted, that the inch calibrations recited may be modified to include, also, the metric scale.

In use for shoulder rotation, which is a condition where the upper part of the body has a slight twist, causing a person to appear off-center, the yoke 19 is set to the height of the individual, on both sides of the body, by set screw 20, and yoke 19 can also be rotated until one of the pins 27 is directly over a shoulder joint, so that, when lowered, pin 27 will touch the acromium process. When upper yoke 19 has been positioned as above described, a measurement in degrees is taken by its degree calibrations, which is done on both sides of the body.

Once shoulder height has been established, pin 25 is adjusted to the width of the shoulder from the center point to the acromium process, and the arms 21 of upper yoke 19 are calibrated in sixteenths of an inch, to establish the width of each shoulder joint, since widths will differ from person to person. Pin 27 is also calibrated in sixteenths of an inch, to sit down on the acromium process of the shoulder joint. Since the pins 27 are calibrated, and will adjust upward or downward, instrument 10 is capable of enabling the user to determine the height and difference of each shoulder of a person.

The kinds of spine deviations, which instrument 10 will measure, are Scoliosis, Kyphosis, and Lordosis, and the headed pins 37 are rotated inward or outward of post 12, so as to touch on the vertebrae of the entire length of the spinal column of a person. In the above-mentioned manner, the height or length of the spinal column can be measured by the calibrations 15, and the pins 37 are calibrated, so as to enable the examiner to determine how deep, and by how much, is the condition of Lordosis.

In pelvic tilt and rotation, this condition is the difference between the right side of the pelvic bone, as opposed to the left side. The lower yoke 29 is lowered or elevated by its set screw 30, so as to locate the exact position of the ilium section of the pelvic bone. Once this position is determined, pins 36 can be set directly over the ilium crest. After the above is accomplished, the examiner will then be able to record the exact difference in height of each side, plus the rotation, since lower yoke 29 is also calibrated in degrees of angle.

It shall also be noted that, because all of the heretofore described elements of instrument 10 are adjustable, a researcher will be able to record the exact differences in body deviations, in inches and in degrees, for further study.

While various changes may be made in the detail construction, it is understood that such changes will be within the spirit and scope of the present invention, as is defined by the appended claims.

What is claimed as new is:

1. A postureometer medical measuring instrument, comprising, in combination, a base member, an upright post mounted upon said base member, said post being cylindrical and hollow and additionally including a linear measurement along its length, an upper and a lower "C" yoke being each affixed by a set screw in selected locations along said calibrated post, a pair of angled arms affixed to each said yoke and extending horizontally therefrom, each said yoke being degree calibrated for rotational adjustment around said post, an outward end of each said arm being linearally calibrated and a first block being adjustably mounted along a length of said outward end of each said arm, a linearally calibrated first pin adjustably supported in said first block, a second block affixed on an end of said first pin and a linearally calibrated second pin adjustably supported in said second block; said first pins of said upper yoke extending horizontally while said second pins thereof extend vertically, and said first pins of said lower yoke extend vertically and said second pins thereof extend horizontally.

2. The combination as set forth in claim 1, wherein a row of horizontally extending, headed pins along a length of said post are adjustable in protrusion therefrom for measuring a contour of a spinal column.

* * * * *